United States Patent
Garbark et al.

(10) Patent No.: US 11,168,284 B2
(45) Date of Patent: Nov. 9, 2021

(54) LAUNDRY BUILDERS AND SURFACTANTS DERIVED FROM BIO-BASED HYDROXYACIDS AND EPOXIDES

(71) Applicant: Battelle Memorial Institute, Columbus, OH (US)

(72) Inventors: Daniel B. Garbark, Blacklick, OH (US); Jeffrey T. Cafmeyer, Columbus, OH (US); Ramanathan S. Lalgudi, Westerville, OH (US)

(73) Assignee: Battelle Memorial Institute, Columbus, OH (US)

( * ) Notice: Subject to any disclaimer, the term of this patent is extended or adjusted under 35 U.S.C. 154(b) by 171 days.

(21) Appl. No.: 16/216,453

(22) Filed: Dec. 11, 2018

(65) Prior Publication Data
US 2019/0177655 A1  Jun. 13, 2019

Related U.S. Application Data (60) Provisional application No. 62/597,273, filed on Dec. 11, 2017.

(51) Int. Cl.
| | | |
|---|---|---|
| C11C 3/00 | (2006.01) | |
| C07C 67/31 | (2006.01) | |
| C07C 237/06 | (2006.01) | |
| C07C 69/704 | (2006.01) | |
| C07C 237/20 | (2006.01) | |

(Continued)

(52) U.S. Cl.
CPC ............ *C11C 3/003* (2013.01); *C07C 67/31* (2013.01); *C07C 69/704* (2013.01); *C07C 237/06* (2013.01); *C07C 237/20* (2013.01); *C11C 3/006* (2013.01); *C11D 1/42* (2013.01); *C11D 1/662* (2013.01); *C11D 1/667* (2013.01); *C11D 1/721* (2013.01); *C11D 1/74* (2013.01); *C11D 1/83* (2013.01); *C11D 1/06* (2013.01); *C11D 1/28* (2013.01); *C11D 1/66* (2013.01)

(58) Field of Classification Search
CPC ...... C07C 69/704; C07C 237/06; C11C 3/006
See application file for complete search history.

(56) References Cited

U.S. PATENT DOCUMENTS

| | | |
|---|---|---|
| 3,138,566 A | 6/1964 | Heinz |
| 2003/0171241 A1* | 9/2003 | Henneberry ............. C09D 7/20 510/417 |

(Continued)

FOREIGN PATENT DOCUMENTS

CA          731107 A          3/1966

OTHER PUBLICATIONS

International Search report from corresponding PCT application No. PCT/US2018/964945, dated Mar. 6, 2019.

(Continued)

*Primary Examiner* — Necholus Ogden, Jr.
(74) *Attorney, Agent, or Firm* — Greer, Burns & Crain, Ltd.

(57) ABSTRACT

Fatty acid based surfactants and methods for producing fatty acid based surfactants are described. The method includes reacting a fatty acid ester epoxide with a hydroxy acid, a hydroxy ester, a polyoxyalkyl diol, or a polyamine. Any remaining esters from the original fatty acid ester epoxide or hydroxy ester can optionally be hydrolyzed. Methods for making citric acid derived surfactants are also described.

14 Claims, 10 Drawing Sheets

(51) Int. Cl.
*C11D 1/72* (2006.01)
*C11D 1/74* (2006.01)
*C11D 1/83* (2006.01)
*C11D 1/42* (2006.01)
*C11D 1/66* (2006.01)
*C11D 1/28* (2006.01)
*C11D 1/06* (2006.01)

(56) References Cited

U.S. PATENT DOCUMENTS

2011/0197915 A1\* 8/2011 Frenkel .................... C11D 3/43
   134/6
2017/0044090 A1\* 2/2017 Benecke ................. C11C 3/003

OTHER PUBLICATIONS

Piispanen, Peter S., Synthesis and Characterization of Surfactants Based on Natural Products, Forskningsrapport 2002:71.
International Preliminary Report on Patentability from corresponding PCT application No. PCT/US2018/964945, dated Jun. 16, 2020.

\* cited by examiner

LAUNDRY BUILDERS AND SURFACTANTS DERIVED FROM BIO-BASED HYDROXYACIDS AND EPOXIDES

This application claims the benefit of U.S. Provisional Patent Application Ser. No. 62/597,273 filed Dec. 11, 2017, which is hereby incorporated by reference in its entirety.

BACKGROUND

Bio-based poly-acids have great opportunity for use in a variety of applications. One application is in chelation such as laundry detergent builders. Detergent builders are water softeners which bind metal cations that also work to maintain detergent stability, help keep soil from redepositing during washing, and improve the cleaning efficiency of the detergent formulation. Standard materials used as detergent builders include sodium triphosphate (STP) and ethylenediaminetetraacetic acid (EDTA). Regulations have pushed for reduction of phosphates used in detergents which has resulted in greater interest in identifying and developing environmentally friendly alternatives.

Another application for bio-based polyacids is in the production of new biobased surfactants for areas such as laundry detergent, personal care, cleaners, and oil field applications.

Laundry detergent surfactants are also referred to as "surface-active agents." Surfactants are ingredients in detergents and many other high-volume products. Surfactants have unique properties which allow the ingredient to be compatible with water and at the same time be attracted to organic materials, such as grease and dirt. Surfactants perform a balancing act of being attracted to the grease and dirt (lipophilic) while also being attracted to water (hydrophilic). Water alone will not adequately clean the laundry. The lipophilic tail is attracted to the grease and dirt while the hydrophilic head group is attracted to the water. The surfactant suspends the grease and dirt in the water so that it can be rinsed away. Therefore, the surfactant performs the primary cleaning function for a laundry detergent.

There are four categories of surfactants: anionic, nonionic, cationic, and amphoteric.

Anionic surfactants are the largest group, accounting for approximately 40% of the world's surfactant production. These products exhibit superior wetting and emulsifying properties and tend to be higher-foaming materials. Fatty acid soaps and alkylbenzene sulfonates fall into this category. Fatty acid soaps typically have a hydrophilic-lipophilic balance (HLB) of approximately 15, which means they function more as a cleaning agent than as a surfactant. Alkylbenzene sulfonates are petroleum based and do not biodegrade under anaerobic conditions.

Nonionic surfactants are the second largest group by a volume at about 35% of the world's surfactant manufacture. Alcohol ethoxylates fall into this category. Although ethoxylates have a wide range of potential HLB values, products such as alkylphenol ethoxylate are an environment concern due to the production of toxic byproducts from biodegradation.

Cationic surfactants typically have excellent antibacterial properties, provide good corrosion protection, and can be good demulsifiers. Quaternary ammonium compounds and pyridines fall into this category.

Finally, amphoteric surfactants can behave as a cation or anion depending on pH. These surfactants, for example phosphatides, such as lauroamphoacetates, have low reactivity with other materials and are increasingly used in personal care products such as baby shampoo and facial cleanser.

The two surfactants of most interest in laundry detergents are anionic and nonionic because they represent almost 75% of the world's production of surfactants.

Therefore, there remains a need for alternate surfactants.

DETAILED DESCRIPTION

Broadly, methods for the conversion of biobased oils to generate highly functionalized surfactants for various applications are described. Methods to utilize epoxidized vegetable oils (e.g. soybean oil, olive oil, canola oil, sunflower oil), animal oils (e.g., tallow or fish oils), algal oils, or mixtures of free fatty acid esters (e.g., mixtures of individual fatty acid esters or combinations of various feedstocks of fatty acid esters) as a platform chemical to produce a wide array of surfactants with unique functionalities have been developed. The chemistry can be applied generally to any fatty acid-based feedstock, but is generally more advantageous with oils high in oleic acid content.

High oleic soybean fatty acid derivatives can perform well as surfactants in laundry detergent applications. The high oleic soybean oil (HOSO) surfactants developed provide improved formulations and performance in laundry applications. They are also anticipated to have better environmental sustainability with increased biodegradability.

One aspect of the invention is a method for producing a fatty acid based surfactant. In one embodiment, the method comprises reacting a fatty acid ester epoxide with a hydroxy acid, a hydroxy ester, a polyoxyalkyl diol, or a polyamine.

In some embodiments, the method further comprises hydrolyzing the ester in the fatty acid ester epoxide or the hydroxy ester under basic conditions.

In some embodiments, the fatty acid ester epoxide is reacted with the hydroxy acid or hydroxy ester and wherein the hydroxy acid or hydroxy ester is a bio-based hydroxy acid or hydroxy ester.

In some embodiments, the fatty acid ester epoxide is reacted with the hydroxy ester and wherein the hydroxy ester contains an alkyl group having 1 to 20 carbon atoms.

In some embodiments, the fatty acid ester epoxide is reacted with the hydroxy acid or the hydroxy ester and the hydroxy acid comprises one or more of citric acid, malic acid, lactic acid, glycolic acid, or tartaric acid, or the hydroxy ester comprises one or more of triethyl citrate, trimethyl citrate, diethyl malate, dimethyl malate, ethyl lactate, methyl lactate, ethyl glycolate, methyl glycolate, ethyl tartrate, or methyl tartrate.

In some embodiments, the fatty acid ester epoxide is reacted with the polyoxyalkyl diol and wherein the polyoxyalkyl diol comprises one or more of diethylene glycol, triethylene glycol, poly(ethylene glycol), dipropylene glycol, tripropylene glycol, or poly(propylene glycol).

In some embodiments, the fatty acid ester epoxide is reacted with the polyamine and wherein the polyamine comprises one or more of ethylene diamine, diethylene triamine, spermidine, spermine, triethylene tetramine, tris (2-aminoethyl)amine, or diaminohexane.

In some embodiments, the fatty acid ester epoxide is formed by epoxidizing a fatty acid ester.

In some embodiments, the fatty acid ester epoxide is derived from a high oleic oil or a mid-oleic oil.

In some embodiments, the fatty acid ester epoxide is derived from one of more of high oleic soybean oil, high oleic algal oil, high oleic olive oil, high oleic canola oil, or high oleic sunflower oil.

In some embodiments, the fatty acid ester epoxide is reacted with the hydroxy acid, the hydroxy ester, the polyoxyalkyl diol, or the polyamine in the presence of a catalyst.

In some embodiments, the catalyst comprises one or more of a tetrafluoroborate catalyst, a metal hydroxide catalyst, or a metal halide catalyst.

In some embodiments, the fatty acid ester epoxide comprises one or more of epoxidized methyl oleate, epoxidized methyl soyate, epoxidized 9-decenoic acid methyl ester, epoxidized soybean oil, epoxidized algal oil, epoxidized algal oil methyl ester, epoxidized olive oil, epoxidized canola oil, or epoxidized sunflower oil.

Another aspect of the invention is a fatty acid based surfactant comprising the reaction product of a fatty acid ester epoxide with a hydroxy ester, a polyoxyalkyl diol, or a polyamine.

In some embodiments, the hydroxy acid comprises one or more of citric acid, malic acid, lactic acid, glycolic acid, or tartaric acid, or the hydroxy ester comprises one or more of triethyl citrate, trimethyl citrate, diethyl malate, dimethyl malate, ethyl lactate, methyl lactate, ethyl glycolate, methyl glycolate, ethyl tartrate, or methyl tartrate.

In some embodiments, the polyoxyalkyl diol comprises one or more of diethylene glycol, triethylene glycol, poly (ethylene glycol), dipropylene glycol, tripropylene glycol, or poly(propylene glycol).

In some embodiments, the polyamine comprises one or more of ethylene diamine, diethylene triamine, spermidine, spermine, triethylene tetramine, tris (2-aminoethyl)amine, or diaminohexane.

In some embodiments, the fatty acid ester epoxide comprises one or more of epoxidized methyl oleate, epoxidized methyl soyate, epoxidized 9-decenoic acid methyl ester, epoxidized soybean oil, epoxidized algal oil, epoxidized algal oil methyl ester, epoxidized olive oil, epoxidized canola oil, or epoxidized sunflower oil.

In some embodiments, the fatty acid ester epoxide is derived from one of more of high oleic soybean oil, high oleic algal oil, high oleic olive oil, high oleic canola oil, or high oleic sunflower oil.

Another aspect of the invention is a method of making a citric acid derived surfactant. In one embodiment the method comprises reacting an alkyl oxide with a citric acid trialkyl ester in the presence of a tetrafluoroborate catalyst.

In some embodiments, the citric acid trialkyl ester containing an alkyl group having 1 to 20 carbon atoms.

In some embodiments, the alkyl oxide comprises one or more of ethylene oxide, propylene oxide, butylene oxide, or butadiene diepoxide.

Replacement of anionic and nonionic surfactants in liquid laundry detergent formulations is one application. However, the same chemistry can be used to produce surfactants for other applications, such as cationic surfactants. Initial evaluation for the surfactants was done in stain removal testing. Anionic surfactants are useful in laundry detergents as they tend to foam, form solids when dry, and produce micelles. Nonionic surfactants tend to be viscous liquids and are excellent in removing oil-based stains.

Alternatives based on the reaction of fatty acid ester epoxides with hydroxylated poly-carboxylic acid esters such as triethyl citrate have been produced.

By biobased oils, we mean vegetable oils, animal fats, or algal oils having at least one triglyceride backbone, wherein at least one fatty acid has at least one double bond.

By fatty acid esters, we mean fatty acids that have been either esterified after steam splitting or hydrolysis of a triglyceride oil or transesterified from a bio-based oil. The fatty acids and esters tend to be mixtures of the fatty acids in the parent oil.

By high oleic oil, we mean an oil with a fatty acid composition where the oleic content is in a range of 70-99 wt %. Examples of high oleic oils include, but are not limited to, high oleic soybean oil, high oleic algal oil, olive oil, high oleic canola oil, and high oleic sunflower oil. By mid-oleic oil, we mean an oil with a fatty acid composition where the oleic content is in a range of 40-70 wt %.

By epoxide, we mean fatty acids or esters that contain an oxirane group at the original olefin site. The epoxidation step can be performed before or after transesterification of the triglyceride backbone.

By hydroxy ester, we mean the ester of hydroxy acids. Examples of hydroxy esters include, but are not limited to, triethyl citrate, trimethyl citrate, diethyl malate, dimethyl malate, ethyl lactate, methyl lactate, ethyl glycolate, methyl glycolate, ethyl tartrate, and methyl tartrate. These esters may also have alkyl chains from $C_1$-$C_{10}$.

By hydroxy acid, we mean hydroxy acids. Examples of hydroxy acids include, but are not limited to, citric acid, malic acid, lactic acid, glycolic acid, and tartaric acid.

By polyamine, we mean a structure that contains diamine or greater. Examples of polyamines include, but are not limited to, ethylene diamine, diethylene triamine, spermidine, spermine, triethylene tetramine, tris (2-aminoethyl) amine, and diaminohexane.

By polyoxyalkyl diol, we mean a diol with an oxyalkyl repeating unit. Example of polyoxyalkyl diols include, but are not limited to, diethylene glycol, triethylene glycol, poly(ethylene glycol), dipropylene glycol, tripropylene glycol, and poly(propylene glycol).

There has recently been great interest in the development of bio-based surfactants for uses from laundry detergents builders (chelators) to oil field applications. One known bio-based chelator is citric acid which has been used for many years to "soften" hard water. However, citric acid is water soluble and requires the addition of a non-polar compound to create a surfactant for other applications. In the past, this has been a problem due to the low reactivity of the tertiary hydroxyl of citric acid. Utilizing salts of tetrafluoroborate allows for the fast and effective reaction of hydroxy acid esters, such as citric and lactic, with epoxides such as epoxidized soybean oil and propylene oxide. Other typical epoxide catalysts, including but not limited to, metal hydroxides or metal halides can also be used.

The approach for synthesizing bio-based hydroxy acids such as citric acid derived detergent builders and surfactants is to build molecular weight through etherification of the unique hydroxyl while maintaining the poly-acid functionality. The poly-acid functionality works as the main chelator serving to "soften" by dissolving the metal ion in the water. The reason for etherification versus esterification of the hydroxyl is hydrolytic stability. The ether bond is much more hydrolytically stable thereby maintaining the desired structure during storage under basic conditions. An ester bond would hydrolyze quickly under basic conditions. Further, by etherifying a hydroxy acid with a fatty acid, a structure that can perform the dual functions of surfactant and chelation is obtained.

Another advantage in reacting with epoxides is that you can vary the carbon chain length. By placing a non-polar chain onto the poly-acid, the surfactant formed will allow for the potential dissolving of greasy materials that are often the cause for poor laundry cleaning. It will also allow for increased miscibility with less polar reactants. By varying the carbon chain length and various functionalities, the hydrophilic-lipophilic balance (HLB) value can be adjusted. The HLB value is typically used to predict the desired application such as hydrophilic surfactants containing a HLB value range of 9-18, water dispersible surfactants HLB range of about 5-9, and hydrophobic surfactants with a HLB range of 0-5. These applications can be divided further but contain some overlap depending on function. Hydrophilic surfactants can be broken into solubilizers (HLB 15-18), detergents (HLB 13-15), and oil/water emulsifiers (HLB 8-16). Water dispersible surfactants include oil/water emulsifiers (HLB 8-16), wetting agents (HLB 7-9), and water/oil emulsifiers (HLB 3-6). Hydrophobic surfactants include water/oil emulsifiers (HLB 3-6) and antifoamers (HLB 2-3). ("Pharmaceutics: The Science of Dosage Form Design" 2nd edition, Michael E. Aulton. Churchill Livingstone, 2002. p. 96.)

Figure 4:
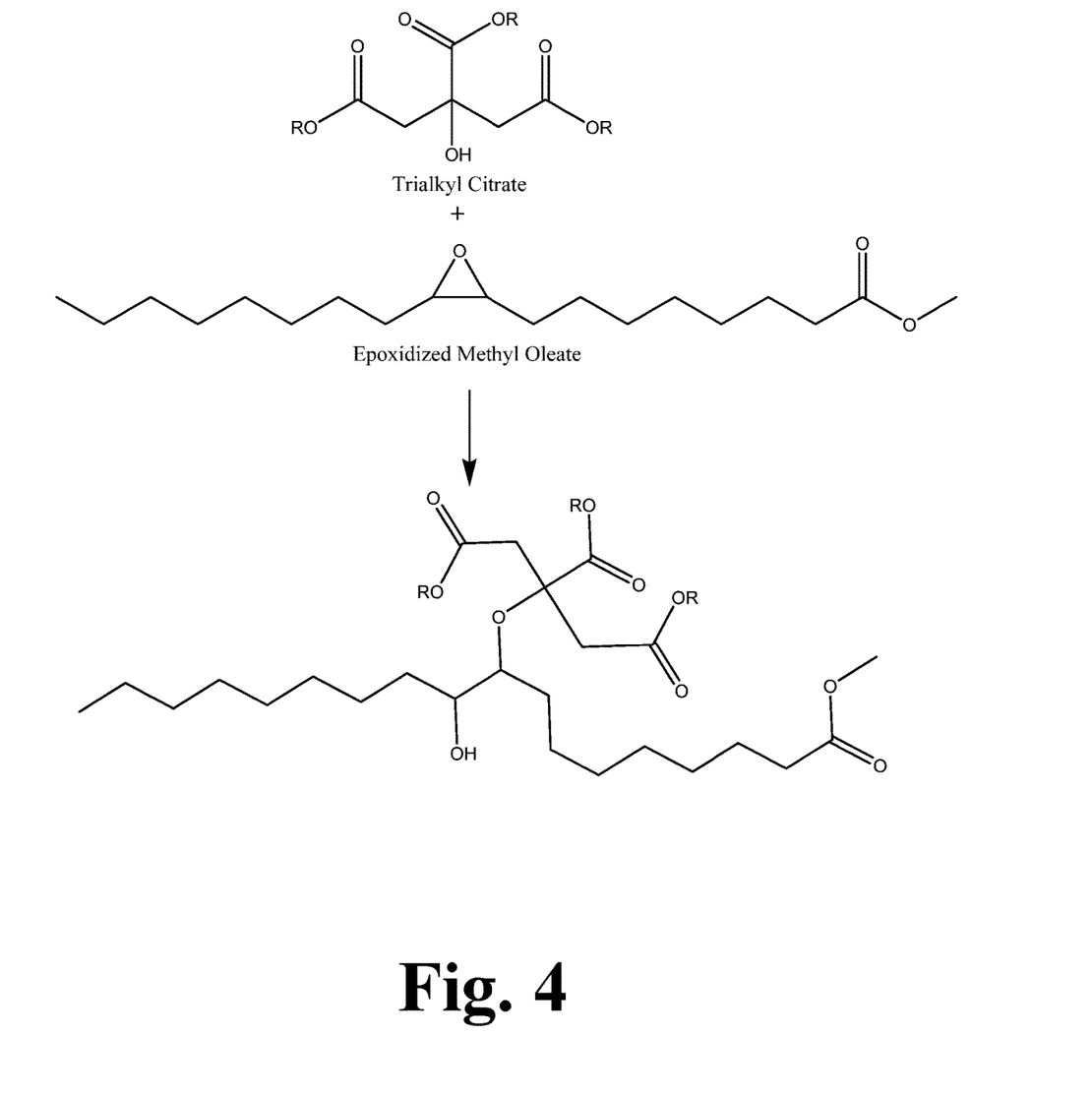
FIG. 4 shows the reaction of triethyl citrate with epoxidized methyl oleate.

As discussed above, these processes can be applied to all epoxidized fatty acid esters. However, when reacting the epoxide with hindered or less active hydroxyls, it is more favorable to use high oleic oils as the feedstock because a reactive hydroxyl is formed when an epoxide ring opens as seen in FIG. 4. In the case of linoleic oils such as standard soybean oil, this hydroxyl is favored to react intra-molecularly with the second epoxide thereby cyclizing into a tetrahydrofuranyl structure. This cyclization would increase further with oils high in linolenic fatty acid. The cyclization reaction is minimized when using biobased oils high in mono-unsaturated fatty acids.

One of the desired products is produced by reacting a fatty acid ester epoxide (such as epoxidized high oleic soybean methyl ester) with a hydroxy acid (such as lactic acid) or a hydroxy ester (such as ethyl lactate) to produce an acid or a poly-ester with an ether functionality. The ester groups from the original fatty acid ester epoxide and those present on the hydroxy ester can optionally be hydrolyzed to the water-soluble salt(s). A second group of products are produced by reacting a fatty acid ester epoxide (such as epoxidized high oleic soybean methyl ester) with a polyoxyalkyl diol (such as triethylene glycol) to produce an ester alcohol with an ether functionality. The ester group from the original fatty acid ester epoxide can optionally be hydrolyzed to the water-soluble salt(s). The water soluble salts from the first and/or second groups of products could optionally be acidified for some applications, if desired. A third group of products are produced by reacting a fatty acid ester epoxide (such as epoxidized high oleic soybean methyl ester) with a polyamine (such as ethylene diamine) to produce a water-soluble surfactant with an amide and amine functionality. The free amine functionalities can optionally be functionalized further by reaction with mono-halide carboxylates (such as mono-chloroacetic acid) to produce chelation functionality.

Figure 6:
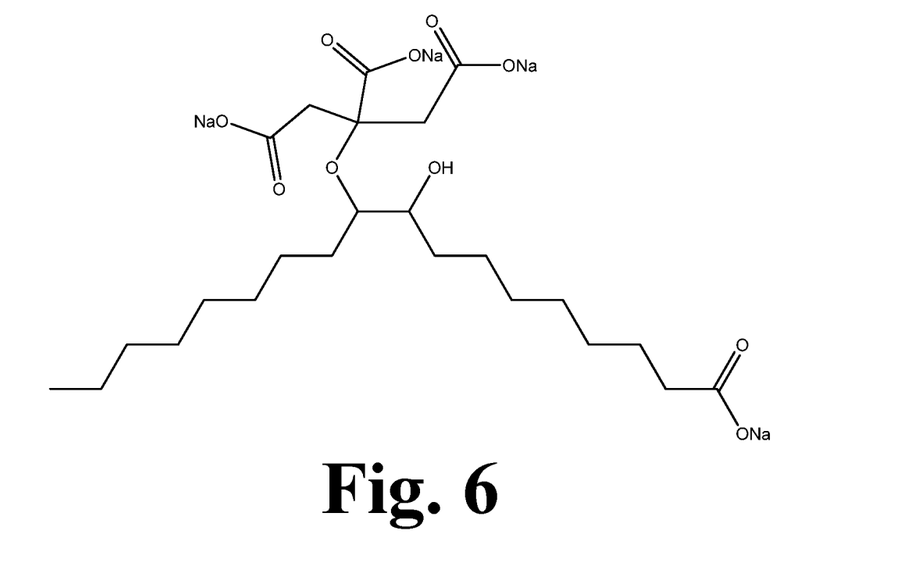
FIG. 6 shows the structure of the reaction product of epoxidized methyl oleate with triethyl citrate after basic hydrolysis.
Figure 7:
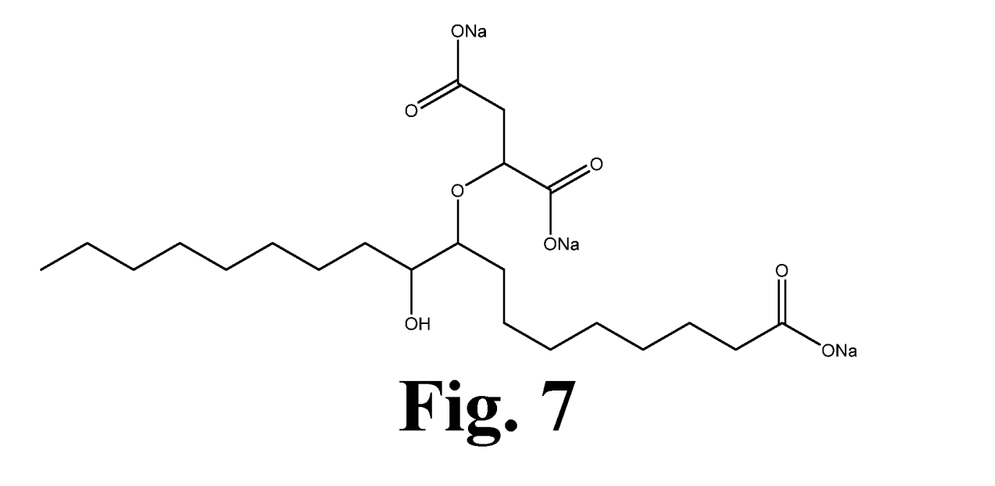
FIG. 7 shows the structure of the reaction product of epoxidized methyl oleate with diethyl malate after basic hydrolysis.
Figure 8:
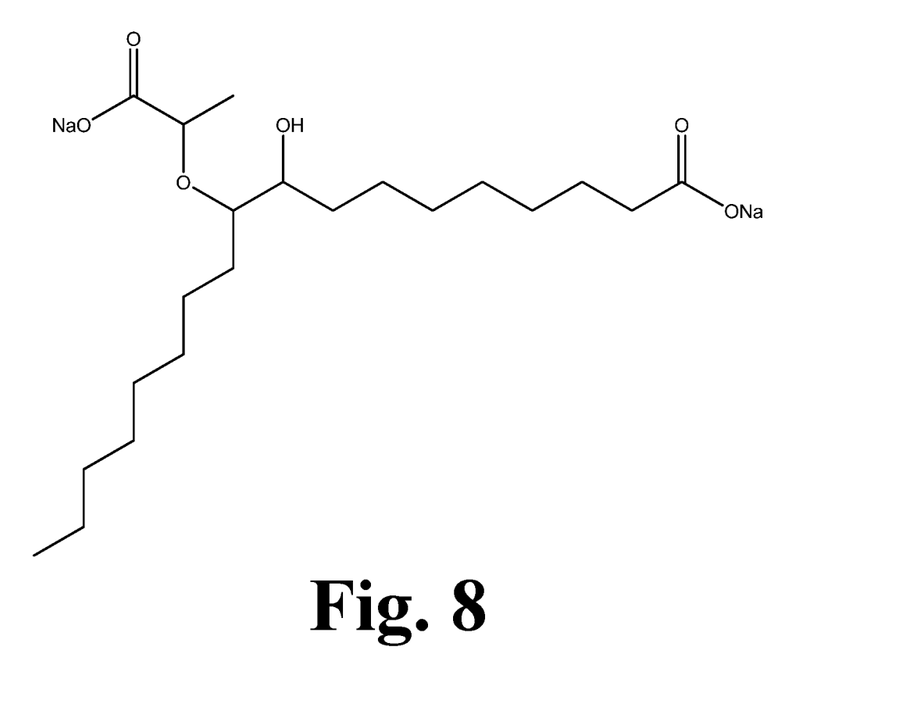
FIG. 8 shows the structure of the reaction product of epoxidized methyl oleate with ethyl lactate after basic hydrolysis.

The initial focus was to determine how hydroxy acid soyate surfactants (those shown in FIGS. 6, 7, and 8) performed in stain removal testing. A standard formulation was obtained, and various amounts of the anionic and nonionic surfactants as seen in Table 1.

TABLE 1

Total Stains Removed by Soy-Based Formulations

| | | Grams of Materials Used | | | | | | | |
|---|---|---|---|---|---|---|---|---|---|
| | Function | Standard | 2 | 3 | 4 | 5 | 6 | 7 | 8 |
| Water | Diluent | 305 | 305 | 305 | 305 | 305 | 305 | 305 | 305 |
| SXS | Hydrotrope | 50 | 50 | 50 | 50 | 50 | 50 | 50 | 50 |
| SDS | Anionic Surfactant | 50 | 25 | 50 | 25 | 25 | | 50 | 50 |
| Ethoxylate | Nonionic Surfactant | | 45 | 45 | | 45 | | | 45 |
| Oleic Citric Ether | Bio-Surfactant | | | | 115 | 70 | 140 | 90 | 45 |
| Oleic Lactic Ether | Bio-Surfactant | 90 | 70 | 45 | | | | | |
| Sodium Carbonate | Builder | 5 | 5 | 5 | 5 | 5 | 5 | 5 | 5 |
| | total = | 500 | 500 | 500 | 500 | 500 | 500 | 500 | 500 |
| | Stains Removed | 301 | 260 | 318 | 300 | 277 | 294 | 324 | 317 |

Figure 9:
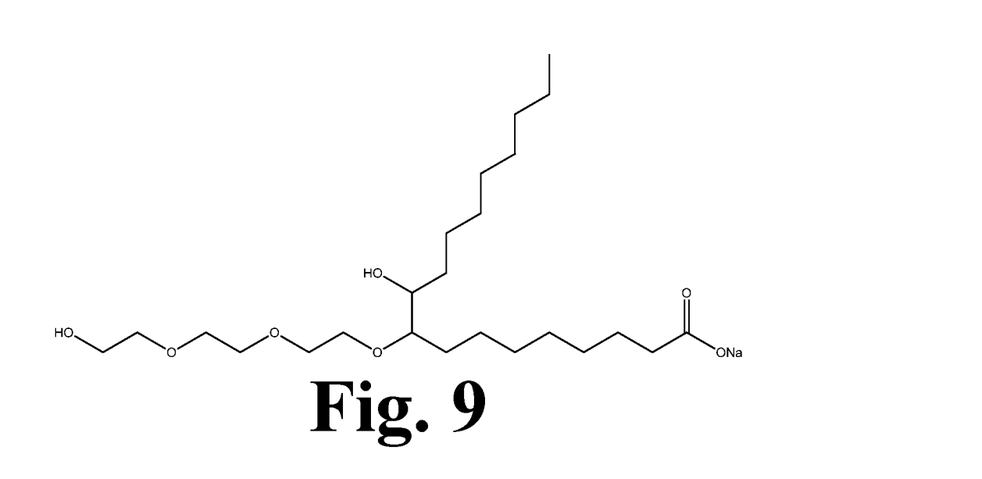
FIG. 9 shows the structure of the reaction product of epoxidized methyl oleate with triethyl ene glycol after basic hydrolysis.

Table 1 reveals that the hydroxy acid soy-based surfactants are effective in removing similar stains compared with nonionic surfactants. Considering specific individual stains, these surfactants improved removal of coffee, cocoa (standard EMPA 112), blood and milk (standard EMPA 116), and red wine stains while showing lower performance in the removal of dust sebum, grass, and make-up stains. These results, combined with other testing, determined that specific functional groups on the fatty acid may be needed depending on the specific use. Grass and make-up stains require sulfonate functionality. For this reason, candidates were produced from high oleic soybean oil that contained both mono- and di-sulfonate functionality as seen in FIGS. 11, 12, 13, and 14. Dust sebum was found to correlate to the fatty acid ethoxylate present in the formulation. Candidates were then synthesized by reacting triethylene glycol or polyethylene glycol 400 (PEG 400) with epoxidized high oleic methyl soyate (FIG. 9). This process could be used with any molecular weight of polyethylene glycol; however, purification would become more difficult with increased molecular weight.

Figure 10:
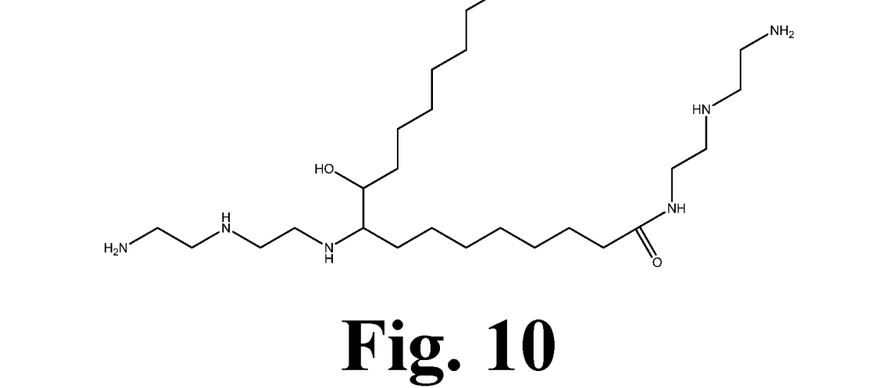
FIG. 10 shows the structure of reaction product of epoxidized methyl oleate with diethylene triamine.
Figure 11:
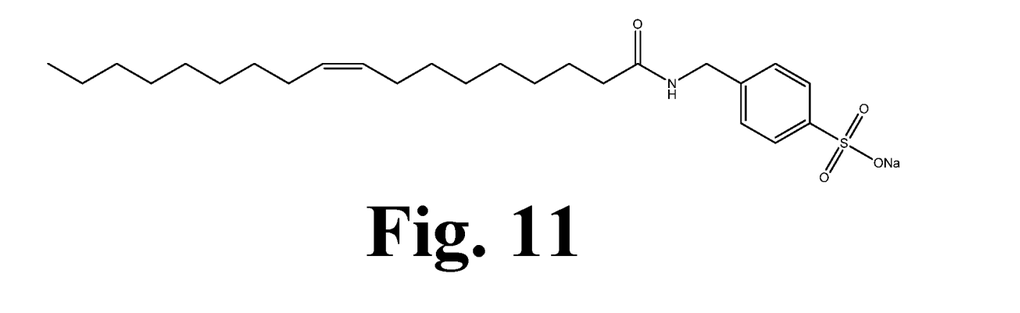
FIG. 11 shows the structure of the sulfonated reaction product of oleic acid benzylamide.
Figure 12:
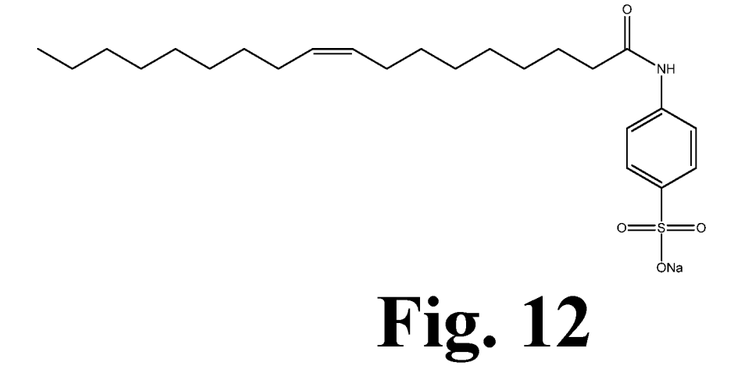
FIG. 12 shows the structure of the sulfonated reaction product of oleic acid aniline amide.
Figure 13:
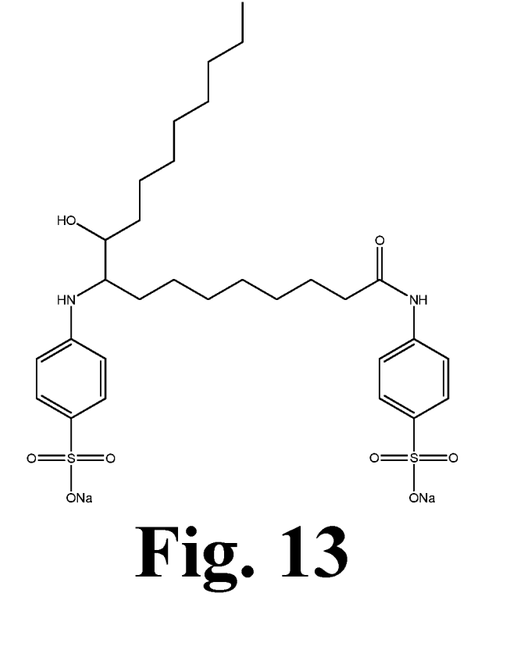
FIG. 13 shows the structure of the reaction product of epoxidized methyl oleate with aniline followed by sulfonation.
Figure 14:
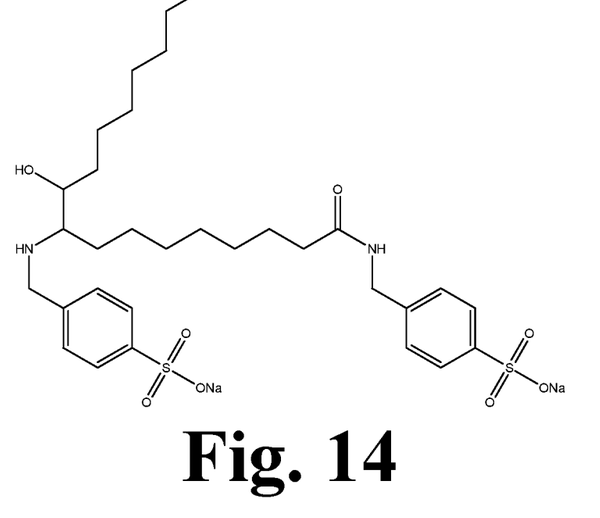
FIG. 14 shows the structure of the reaction product of epoxidized methyl oleate with benzylamine followed by sulfonation.
Figure 15:
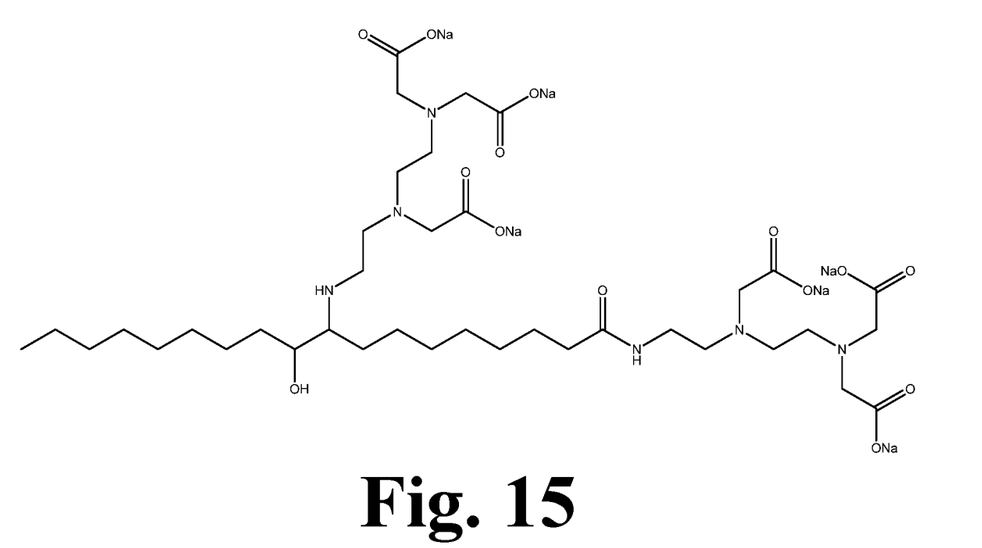
FIG. 15 shows the structure of the reaction product of epoxidized methyl oleate with diethylene triamine that has been functionalized with chloroacetic acid sodium salt.

Another alternative functionality is in the production of amines. Amines can facilitate pH control and removal of fatty acid ester-based stains. The reaction of diethylene triamine (FIG. 10) or ethylene diamine with epoxidized high oleic methyl soyate allows to produce amine type functionality. This amine functionality can be further reacted with chloroacetic acid to produce a surfactant with builder functionality (FIG. 15).

Finally, most of these reactions can be run by starting with epoxidized triglycerides (as seen in Example 10), but the final formulations will usually include glycerol. The epoxidation of the triglyceride is well known and follows the same procedure seen in Example 2. Epoxidized methyl ester was used as a convenience to faster reaction times and easier analysis to verify complete reactions. Epoxidized methyl ester can be produced by epoxidizing the methyl ester, or transesterifying epoxidized triglycerides with methanol. Various combinations of epoxidized esters may be used.

All examples herein are merely illustrative of typical aspects of the invention and are not meant to limit the invention in any way.

Example 1

Figure 1:
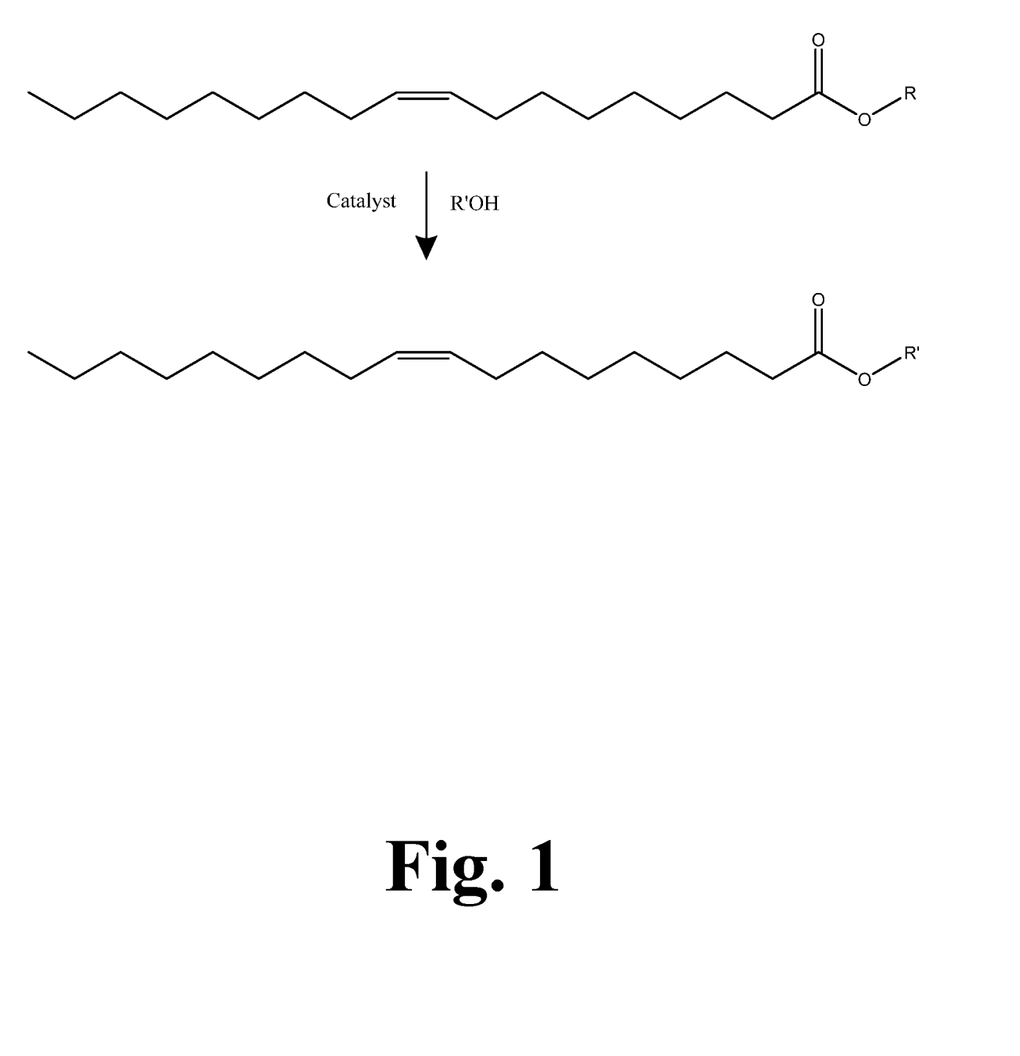
FIG. 1 is a schematic depicting the transesterification of a triglyceride oil with an alcohol.

This example shows a procedure for transesterification of high oleic soybean oil with methanol (FIG. 1).

1400.01 g (1.5954 mol) high oleic soybean oil was added to a flask containing 2320 mL methanol and 6.01 g sodium methoxide. The mixture was heated to reflux for 5 hours. The mixture was partitioned with 500 mL 20% brine and 1 L ethyl acetate. The ethyl acetate was rinsed with a second aliquot of brine and dried with magnesium sulfate. The mixture was filtered, and the solvent was removed by rotovap followed by vacuum at 90° C. at 1.3 mm Hg for 1 hour. The methyl ester product was verified by NMR analysis.

Example 2

Figure 2:
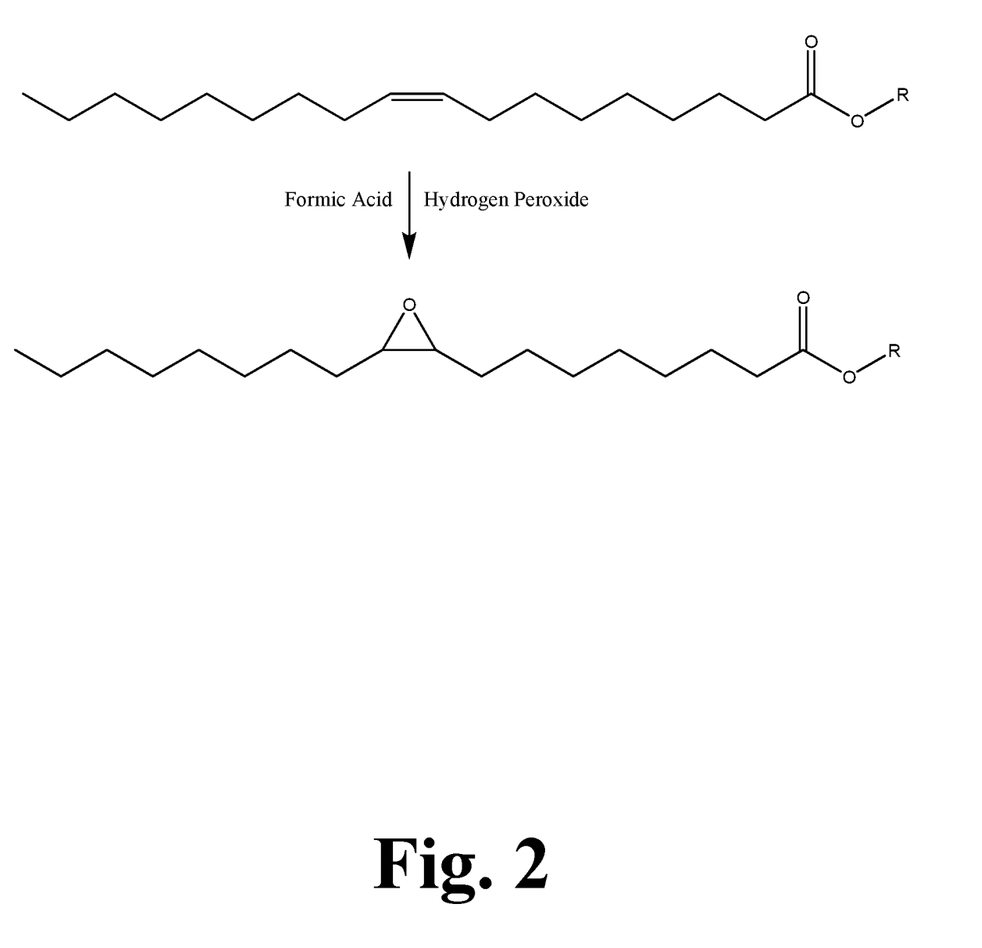
FIG. 2 is a schematic depicting the epoxidation of fatty acid esters.

This example shows a procedure for epoxidation of high oleic methyl soyate (FIG. 2).

1201.10 g (4.0875 mol) high oleic methyl soyate was added to a flask containing 67.12 g (1.458 mol) formic acid and heated to 55° C. 372.72 g (5.479 mol) 50% hydrogen peroxide was weighed into an addition funnel. The hydrogen peroxide was added dropwise over 20 minutes and a heating mantle and ice-water bath were used to maintain a temperature range of 55-60° C. After 2 hours, the reaction was 85% complete. 40 g more 50% hydrogen peroxide were added, and the temperature was held for 4 hours longer. Complete reaction was verified by NMR. The mixture was dissolved into ethyl acetate and transferred to a separatory funnel. The water layer was removed. The ethyl acetate layer was rinsed with saturated sodium bicarbonate until the pH of the water layer became basic. The ethyl acetate layer was dried with magnesium sulfate, filtered, and the solvent was removed by vacuum at 55° C. at 1 mm Hg for 2 hours.

Example 3

Figure 3:
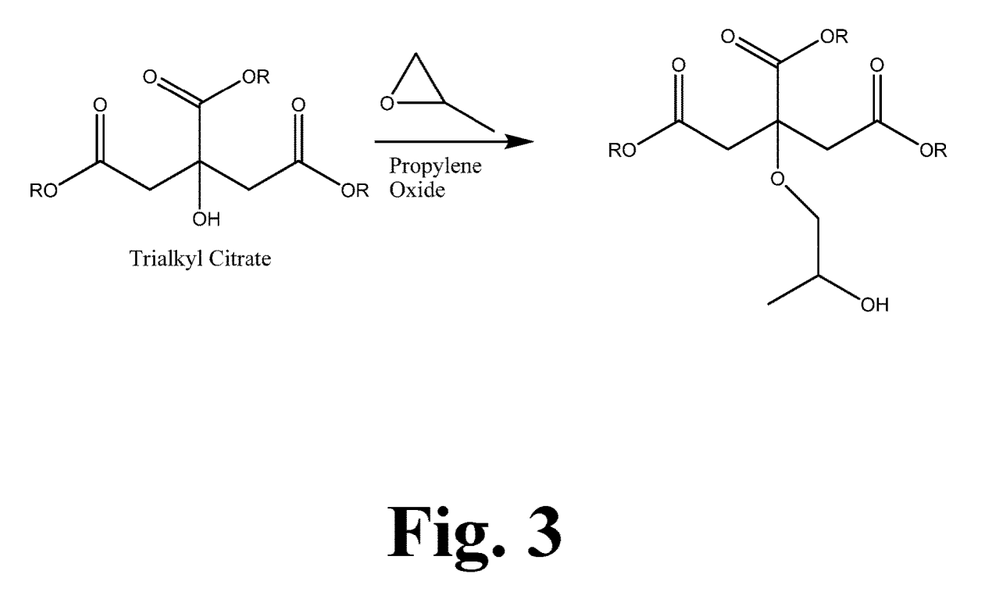
FIG. 3 shows the alkoxylation reaction with citric acid trialkyl ester.

This example shows a procedure for making alkoxylated triethyl citrate (FIG. 3).

20.00 g (0.0274 mol) of triethyl citrate was added to a flask with stirbar and 19.00 g (0.3271 mol) of propylene oxide. A condenser was attached followed by addition of 0.40 g of copper (II) tetrafluoroborate. The reaction was immediately exothermic and began refluxing. The temperature was held at 50° C. externally for 1 hour. NMR analysis revealed complete functionalization of the citrate hydroxyl group.

Example 4

This example shows a procedure for making the etherified product of triethyl citrate and epoxidized methyl oleate.

20.03 g (0.0641 mol) of epoxidized methyl oleate was mixed in a reactor with 15.00 g (0.0543 mol) of triethyl citrate and heated to 50° C. 0.44 g of copper (II) tetrafluoroborate was dissolved into 3.00 g (0.0109 mol) of triethyl citrate and added to the reactor. The reaction was immediately exothermic and reached a maximum temperature of 70.1° C. The reaction was analyzed after 1 hour by proton NMR and shown to be nearly complete. The reaction was stopped after 2 hours of total reaction time.

Scale-Up Example 4

56.40 g (0.1805 mol) of epoxidized methyl oleate was mixed in a reactor with 70.00 g (0.2534 mol) of triethyl citrate and heated to 50° C. 1.04 g of copper (II) tetrafluoroborate was dissolved into 7.01 g (0.0254 mol) of triethyl citrate and added to the reactor. The reaction was immediately exothermic and reached a maximum temperature of 67.7° C. The reaction was stopped after 2 hours of total reaction time.

Example 5

Figure 5:
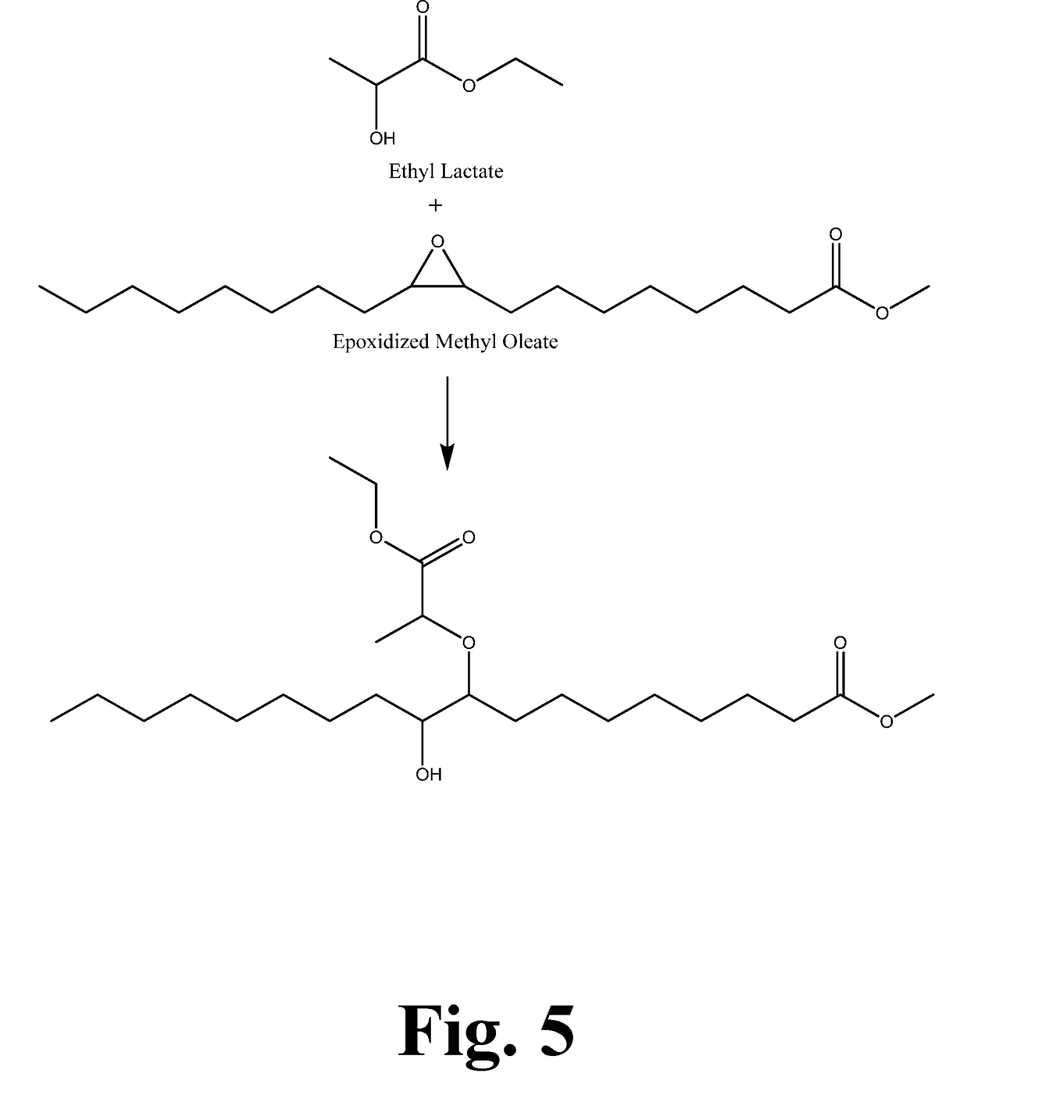
FIG. 5 shows the reaction of ethyl lactate with epoxidized methyl oleate.

This example shows a procedure for making the etherified product of ethyl lactate and epoxidized methyl soyate (FIG. 5).

390.53 g (1.2185 mol) of epoxidized methyl soyate was weighed into a flask containing 271.15 g (2.2954 mol) of ethyl lactate and heated to 55° C. 3.28 g of iron (II) tetrafluoroborate was dissolved into 53.11 g (0.4496 mol) of ethyl lactate and added to the reactor. The reaction was immediately exothermic and reached a maximum temperature of 89.9° C. The reaction was stopped after 8 hours of total reaction time.

Example 6

This example shows a procedure for making the etherified product of diethyl malate and epoxidized high oleic methyl soyate and converting to a final laundry surfactant form.

150.49 g (0.4800 mol) of epoxidized high oleic methyl soyate was weighed into a flask containing 251.05 g (1.3200 mol) of diethyl malate and heated to 55° C. 2.24 g of iron (II) tetrafluoroborate was dissolved into 27.39 g (0.1440 mol) of diethyl malate and added to the reactor. The reaction was immediately exothermic and reached a maximum temperature of 77.8° C. The reaction was stopped after 4 hours of total reaction time. The product was passed through a bed of basic alumina. Excess diethyl malate was removed by vacuum at 140° C. and 1 mm Hg for 2 hours resulting in an ether-triester oil.

38.93 g (0.9733 mol) sodium hydroxide was dissolved into 160.08 g of water heated to 95° C. 160 g (0.9549 mol ester) of the ether-triester oil was added dropwise over 120 minutes. The mixture was thickening, so 22.93 g more water was added. NMR spectroscopy revealed hydrolysis of the esters to carboxylate salts.

Example 7

This example shows a procedure for making the etherified product of triethylene glycol and epoxidized high oleic methyl soyate and converting to a final laundry surfactant form. This process was also repeated with PEG 400 to produce a second ethoxylate ether.

52.54 g (0.1681 mol) of epoxidized high oleic methyl soyate was weighed into a flask containing 51.27 g (0.3414 mol) of triethylene glycol and heated to 50° C. 0.55 g of copper (II) tetrafluoroborate was dissolved into 11.11 g (0.0740 mol) of triethylene glycol and added to the reactor. The reaction was slowly exothermic and reached a maximum temperature of 56.1° C. but was two phases. After 20 minutes, the temperature was raised to 70° C. after which the reaction was exothermic to a maximum of 81.0° C. Reaction was complete after 1 hour. The oil was dissolved into ethyl acetate and partitioned three times with water. The ethyl acetate was dried with magnesium sulfate. This process was repeated a second time to increase the mass available. The runs were combined and filtered through a medium frit. Excess ethyl acetate was removed by vacuum first in a rotovap and second at 70° C. and 3 mm Hg resulting in a yellow ether-monoester oil. NMR spectroscopy verified production of the water insoluble product.

10.37 g (0.2593 mol) sodium hydroxide was dissolved into 20.33 g of water and added to 120 g (0.2593 mol ester) of the ether-monoester oil. The temperature was raised to 95° C. for 2 hours. IR confirmed only trace ester was present. The reaction was run 30 minutes longer at 98° C. The final water-soluble product was stored in a jar.

Example 8

This example shows a procedure for making an amine functional product of diethylene triamine (DET) and epoxidized high oleic methyl soyate.

38.97 g (0.3777 mol) of DET was weighed into a flask and heated to 55° C. 54.13 g (0.1732 mol) of epoxidized high oleic methyl soyate was weighed into an addition funnel and added dropwise over 20 minutes to the warm DET with stirring for 4 hours. Only a small amount reacted, so the temperature was raised to 65° C. for 4 hours and then to 70° C. for 4 hours more. NMR revealed 25% of the epoxy had reacted and 66% of the methyl ester had amidified. 19.64 g (0.1904 mol) DET was added, and the mixture was heated to 160° C. for 4 hours, followed by 170° C. for 2.5 hours. Reaction was then complete. Excess DET was removed by vacuum at 90 C and 1.1 mm Hg for 2.5 hours, resulting in a water-soluble amine functional oil.

Example 9

This example shows a procedure for further functionalizing the product from Example 8.

5.25 g (0.0108 mol) of amine functional oil was added to a flask containing 5.27 g (0.1318 mol) sodium hydroxide and 17.00 g water. 6.25 g (0.0661 mol) chloroacetic acid was then added slowly. The temperature was held at 70° C. for 4 hours. NMR analysis supported the addition of carboxymethyl functionalization.

Example 10

This example shows an alternative approach to produce the surfactant in Example 8.

49.93 g (0.0535 mol) of epoxidized high oleic soybean oil was added to 66.33 g (0.6429 mol) diethylene triamine and heated with stirring to 180° C. The reaction was held for 12 hours. The amidification was verified by IR. The water-soluble product was verified by NMR analysis.

Example 11

This example shows a procedure for the amidification of high oleic soybean fatty acids with an aromatic amine.

194.83 g (0.6961 mol) high oleic soybean fatty acid was added to a reactor containing 72.82 g (0.7819 mol) aniline and heated with stirring to 200° C. After 2 hours, 15.85 g more aniline was added to the reactor. At 4 hours, the reaction was 96% complete. The reactor was heated to 230° C. with 0.5 SCFH argon headspace flow to distill excess aniline. The remainder of aniline was then removed by vacuum at 110° C. at 1 mm Hg for 3 hours.

Example 12

This example shows a procedure for the sulfonation of the aromatic amide produced in Example 11.

50.16 g (0.1403 mol) of the aniline product from Example 11 was weighed into a flask. 126.5 g (0.4738 mol) of fuming sulfuric acid, 30% trioxide was added dropwise while controlling the temperature below 60° C. Once addition was complete, the reaction was held at 70° C. for 3 hours. NMR analysis supported the sulfonated aromatic amide structure.

Example 13

This example shows an alternative procedure to produce the surfactant produced in Example 12.

74.99 g (0.2552 mol) high oleic methyl soyate was weighed into a flask with 49.81 g (0.2552 mol) sulfanilic acid sodium salt and 196.82 g N-methylpyrrolidinone (NMP). The reaction was heated with stirring to 170° C. for 12 hours followed by 190° C. for 2 hours. The NMP was removed by vacuum distillation.

Example 14

This example shows a procedure for the reaction of benzylamine with epoxidized high oleic methyl soyate.

151.18 g (0.4838 mol) high oleic methyl soyate was added to an autoclave containing 131.05 g (1.2229 mol) benzylamine and 1.35 g zinc chloride. The reactor was heated to 200° C. for 2 hours, after which IR showed the reaction was nearly complete. 17.95 g (0.1675 mol) benzylamine was added and the reaction continued for 3 hours more. IR showed complete reaction. The mixture was transferred to a flask and excess benzylamine was removed by vacuum at 115° C. at 1.1 mm Hg for 2 hours. NMR analysis supported the aromatic amide structure.

Example 15

This example shows a procedure for the sulfonation of the product from Example 14.

25.60 g (0.0517 mol) of the benzylamide product from Example 14 was weighed into a flask and heated to 40° C. with stirring. 46.37 g (0.1564 mol) of fuming sulfuric acid, 27% trioxide was added dropwise while controlling the temperature at 70° C. NMR supported the sulfonated amide structure.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for producing a fatty acid based surfactant comprising:
    reacting a fatty acid ester epoxide with a hydroxy acid in the presence of a tetrafluoroborate salt catalyst or a metal hydroxide catalyst to produce an acid with an ether functionality, a hydroxy ester in the presence of a tetrafluoroborate salt catalyst, a metal hydroxide catalyst, or a metal halide catalyst to produce a poly-ester with an ether functionality, a polyoxyalkyl diol in the presence of a tetrafluoroborate salt catalyst or a metal hydroxide catalyst to produce an ester alcohol with an ether functionality, or a polyamine in the presence of a tetrafluoroborate salt catalyst, a metal hydroxide catalyst, or a metal halide catalyst to produce an amide with an amine functionality, wherein the polyamine is ethylene diamine, spermidine, tris (2-aminoethyl)amine, or diaminohexane.

2. The method of claim 1 further comprising hydrolyzing the ester from the fatty acid ester epoxide or the hydroxy ester under basic conditions.

3. The method of claim 1 wherein the fatty acid ester epoxide is reacted with the hydroxy ester and wherein the hydroxy ester contains an alkyl group having 1 to 20 carbon atoms.

4. The method of claim 1 wherein the fatty acid ester epoxide is reacted with the hydroxy acid or hydroxy ester and wherein the hydroxy acid comprises one or more of citric acid, malic acid, lactic acid, glycolic acid, or tartaric acid, or wherein the hydroxy ester comprises one or more of triethyl citrate, trimethyl citrate, diethyl malate, dimethyl malate, ethyl lactate, methyl lactate, ethyl glycolate, methyl glycolate, ethyl tartrate, or methyl tartrate.

5. The method of claim 1 wherein the fatty acid ester epoxide is reacted with the polyoxyalkyl diol and wherein the polyoxyalkyl diol comprises one or more of diethylene glycol, triethylene glycol, poly(ethylene glycol), dipropylene glycol, tripropylene glycol, or polypropylene glycol).

6. The method of claim 1 wherein the fatty acid ester epoxide is formed by epoxidizing a fatty acid ester.

7. The method of claim 1 wherein the fatty acid ester epoxide is derived from a high oleic oil or a mid-oleic oil.

8. The method of claim 1 wherein the fatty acid ester epoxide is derived from one of more of high oleic soybean oil, high oleic algal oil, high oleic olive oil, high oleic canola oil, or high oleic sunflower oil.

9. The method of claim 1 wherein the fatty acid ester epoxide comprises one or more of epoxidized methyl oleate, epoxidized methyl soyate, epoxidized 9-decenoic acid methyl ester, epoxidized soybean oil, epoxidized algal oil, epoxidized algal oil methyl ester, epoxidized olive oil, epoxidized canola oil, or epoxidized sunflower oil.

10. The method of claim 1 wherein the fatty acid ester epoxide is derived from one of more of high oleic soybean oil, high oleic algal oil, high oleic olive oil, high oleic canola oil, or high oleic sunflower oil.

11. A method of making a citric acid derived surfactant comprising:
    reacting an alkyl oxide with a citric acid trialkyl ester in the presence of a tetrafluoroborate catalyst.

12. The method of claim 1 wherein the fatty acid ester is reacted with the hydroxy acid.

13. The method of claim 1 wherein the fatty acid ester is reacted with the hydroxy ester.

14. The method of claim 1 wherein the fatty acid ester is reacted with the polyamine.

* * * * *